(12) United States Patent
Hölscher et al.

(10) Patent No.: US 6,593,105 B1
(45) Date of Patent: Jul. 15, 2003

(54) PRION PROPAGATION INHIBITION BY DOMINANT-NEGATIVE PRION PROTEIN MUTANTS

(75) Inventors: Christina Hölscher, Heidelberg (DE); Alexander Bürkle, Leimen (DE)

(73) Assignee: Deutsches Krebsforschungszentrum Stiftung des Offentilichen Rechts, Heidelberg (DE)

(*) Notice: Subject to any disclaimer, the term of this patent is extended or adjusted under 35 U.S.C. 154(b) by 0 days.

(21) Appl. No.: 09/367,572

(22) PCT Filed: Feb. 13, 1998

(86) PCT No.: PCT/DE98/00429

§ 371 (c)(1),
(2), (4) Date: Nov. 3, 1999

(87) PCT Pub. No.: WO98/36059

PCT Pub. Date: Aug. 20, 1998

(30) Foreign Application Priority Data

Feb. 14, 1997 (DE) .................................. 197 05 786

(51) Int. Cl.[7] ........................ C12N 15/00; C12N 15/63; C12N 5/00; C07H 21/04
(52) U.S. Cl. .................. 435/69.1; 435/320.1; 435/325; 435/455; 536/23.5
(58) Field of Search .............................. 435/320.1, 325, 435/69.1, 455; 536/23.5

(56) References Cited

FOREIGN PATENT DOCUMENTS

| WO | WO 9311155 | 6/1993 |
|---|---|---|
| WO | WO 9639834 | 12/1996 |

OTHER PUBLICATIONS

Ngo et al., Computational Complexity Protein Structure Prediction and the Levinthal Paradox, 1994, pp. 491–495.*
Rudinger et al., Charateristics of the amino acids as components of a peptide hormorme sequence, Jun. 1976, Biological Council, pp. 1–7.*
Bowie et al., Deciphering the Message in Protein Sequence Tolerance to Amino Acid Substitutions, Mar. 1990, Science, vol. 247, pp. 1306–1310.*
Muramoto, et al., "Recombinant Scrapie–Like Prion Protein of 106 Amino Acids is Soluble" Proc. Natl. Acad. Sci., vol. 93, pp 15457–15462, 1996.
Priola, et al., "Heterologuous PrP Molecules Interfere with Accumulation of Protease–Resistant PrP in Scrapie–Infected Murine Neuroblastoma Cells" J. of Virology, pp. 4873–4878, 1994.
Warwicker, et al., "A model for Prion Protein Dimerisation Based on α–Helical Packing" Biochemical and Biophysical Research Communications vol. 226, pp. 777–782, 1996.
Gasset, et al., "Predicted α–Helical Regions of the Prion Protein when Synthesized as Peptides form Amyloid" Proc. Natl. Acad. Sci., vol. 89, pp. 10940–10944, 1992.
Baldwin, et al., "Prion Protein Isoforms, a Convergence of Biological and Structural Investigations" J. of Biological Chemistry, vol. 270, No. 33, pp. 19197–19200, 1995.
Nguyen, et al., "Prion Protein Peptides Induce α–Helix to β–Sheet Conformational Transitions" Biochemistry vol. 34, pp. 4186–4192, 1995.
Hölscher, et al., "Overexpression of Nonconvertible PrP$^c$ Δ114–121 in Scrapie–Infected Mouse Neuroblastoma Cells Leads to Trans–Dominant Inhibition of Wild–Type PrP$^{Sc}$ Accumulation" J. of Virology, pp. 1153–1159,1997.
Mehlhorn, et al. "High–Level Expression and Characterization of a Purified 142–Residue Polypeptide of the Prion Protein" Biochemistry, vol. 35 No. 17, pp. 5528–5537, 1996 Abstract only.
Tumas, et al., "High–frequency Cell Surface Expression of a Foreign Protein in Murine Hematopoietic Stem Cells Using a New Retroviral Vector" Blood, vol. 87, No. 2, pp. 509–517, 1996 Abstract only.
Krasemann, et al., "Induction of Antibodies against Human Prion Proteins (PrP) by DNA–Mediated Immunization of PrP0/0 Mice" J. Immunol. Methods, vol. 199 No. 2, pp. 109–118,1996 Abstract only.
Krasemann, et al. DNA Vaccination with Human Prion Genes Induces Antibodies Against Prion Proteins in PrP0/0 Mice, 1995 Abstract only Vaccines 96: 13 Meet. Mol. Approch to Cont. Infet. Meeting date 1995.

* cited by examiner

Primary Examiner—Ram R. Shukla
(74) Attorney, Agent, or Firm—Steven J. Hultquist; Marianne Fuierer; Yongzhi Yang

(57) ABSTRACT

The present invention relates to a vector which is suitable for gene prophylaxis/gene therapy, containing a nucleic acid fragment coding for a mutated prion protein. The invention further relates to a vaccination agent which contains the vector in addition to the usual auxiliary agents, and to the use of the vector or vaccination agent in the prophylaxis and/or treatment of prion diseases. The invention further relates to non-human mammals, e.g. working animals, which are resistant to prion infections.

14 Claims, 8 Drawing Sheets

Figure 1:
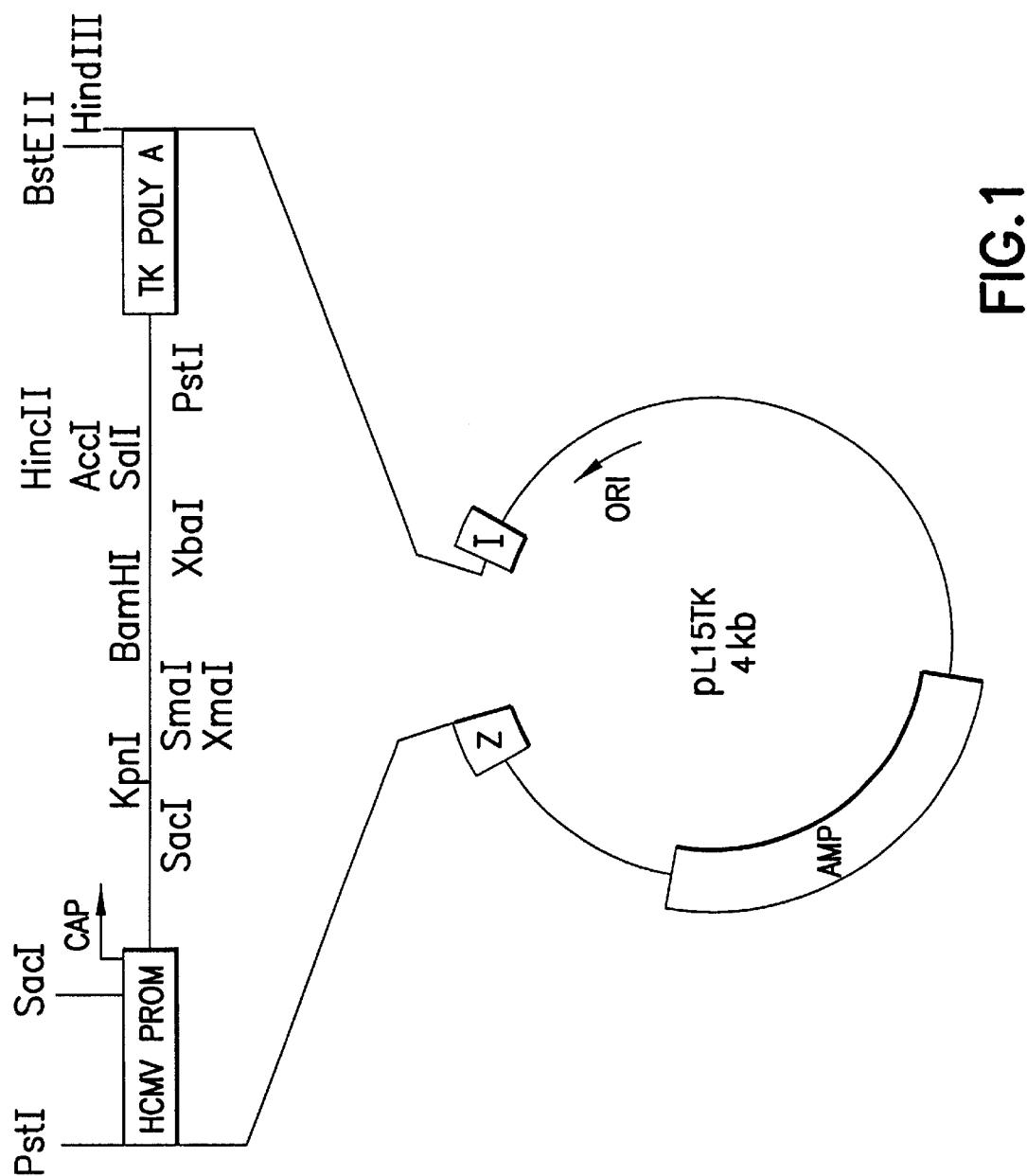

```
  1  AATTCCTTCAGAACTGAACCATTTCAACCGAGCTGAAGCATTCTGCCTTC    50
     ::::::::::::::::::::::::::::::::::::::::::::::::::
  1  xxxxxxxxxxxxxxxxxxxxxxxxxxxxxxxxxxxxxxxxxxxxxxxxxx    50

51  CTAGTGGTACCAGTCCAATTTAGGAGAGCCAAGCAGACTATCAGTCATCA   100
     ::::::::::::::::::::::::::::::::        ||||||||||
 51  xxxxxxxxxxxxxxxxxxxxxxxxxxxxxxxxcgtccagtcatca       100

101  TGGCGAACCTTGGCTACTGGCCTGGCCCTCTTTGTGACTATGTGGACT    150
     ||||||||||||||||||||||||||||||||||||||||||||||||
101  tggcgaaccttggctactggcctggccctctttgtgactatgtggact    150

151  GATGTCGGCCCTCTGCAAAAAGCGGCCAAAGCCTGGAGGGTGGAACACCGG   200
     ||||||||||||||||||||||||||||||||||||||||||||||||||
151  gatgtcggccctctgcaaaaagcggccaaagcctggagggtggaacaccgg   200

201  TGGAAGCCGGTATCCCGGGCAGGGAAGCCCTGAGGCAACCGTTACCCAC    250
     ||||||||||||||||||||||||||||||||||||||||||||||||
201  tggaagtcggtatcccgggcagggaagccctgaggcaaccgttacccac    250
           silent
```

FIG.2A

```
251  CTCAGGGTGGCACCTGGGGCAGCCCCACGGTGGCTGGGGACAACCC  300
     |||||||||||||||||||||||||||||||||||||||||||||
251  ctcagggtggcacctggggcagccccacgtggtggctggggacaaccc  300

301  CATGGGGGGCAGCTGGGGACAACCTCATGGTGTGGTAGTTGGGGTCAGCCCCA  350
     ||||||||||||||||||||||||||||||||||||||||||||||||||||
301  catgggggggcagctggggacaacctcatggtggtagttggggtcagcccca  350

351  TGGCGGTGGATGGGCCAAGGAGGGGTACCCATAATCAGTGGAACAAGC  400
     ||||||||||||||||||||||||||||||||||||||||||||||||
351  tggcggtggatgggccaaggaggggtacccataatcagtggaacaagc  400

401  CCAGCAAACCAAAAACCAACCTCAAGCATGTGGCAGGCTGCGGCAGCT  450
     |||||||||||||||||||||||||||||||||||||||||||||
401  ccagcaaaccaaaaaccaacctcaagcatgtggcagg..........  437

451  GGGGCAGTAGTGGCCTTGGTGGCTACATGCTGGGAGGCGCCATGAG  500
     |||||||||||||||||||||||||||||||||||||||||||||
438  ..........gggtggccttggtggctacatgctggggagcgccatgag  476
             └─silent─┘
```

FIG.2B

```
501  CAGGCCCATGATCCATTTTGGCAACGACTGGGAGGACCGCTACTACCGTG  550
     ||||||||||||||||||||||||||||||||||||||||||||||||||
477  caggcccatgatccatttggcaacgactgggaggaccgctactaccgtg  526

551  AAAACATGTACCGCTACCCTAACCAAGTGTACTACAGGCCAGTGATCAG  600
     ||||||||||||||||||||||||||||||||||||||||||||||||
527  aaaacatgtaccgctaccctaaccaagtgtactacaggccagtgatcag  576

601  TACAGCAACCAGAACAACTTCGTGCACGACTGCGTCAATATCACCATCAA  650
     ||||||||||||||||||||||||||||||||||||||||||||||||||
577  tacagcaaccagaacaacttcgtgcacgactgcgtcaatatcaccatcaa  626

651  GCAGCACACGGTCACCACCACCACCAAGGGGAGAACTTCACCGAGACCG  700
     ||||||||||||||||||||||||||||||||||||||||||||||||
627  gcagcacacggtcaccaccaccaccaaggggagaacttcaccgagaccg  676

701  ATGTGAAGATGATGAGCGTGGTGGAGCAGATGTGCGTCACCCAGTAC  750
     |||||||||||||||||||||||||||||||||||||||||||||||
677  atgtgaagatgatgagcgtggtggagcagatgtgcgtcacccagtac  726
```

FIG. 2C

```
751 CAGAAGGAGTCCCAGGCCTATTACGACGGGAAGATCCAGCAGCACCGT 800
    ||||||||||||||||||||||||||||||||||||||||||||||||
727 cagaaggagtcccagcctattacgacgaggaagatccagcagcaccgt 776

801 GCTTTCTCCCTCCCCTCCCTCCCTGTCATCCTCCTTCATCTTCC 850
    ||||||||||||||||||||||||||||||||||||||||||||
777 gcttttctccctccccctccctcctgtcatcctcctcatcttcc 826

851 TGATCGTGGGGATGAGGAGGCCTTCCCTGTTCCTTCGCATTCTCGGTG 900
    |||||||||||||||||    ||||||||| ||||||| |||||||
827 tgatcgtggggatgaggggagctcggtacccgggg........ 859
                      STOP
```

FIG.2D

| FIG.2A |
|--------|
| FIG.2B |
| FIG.2C |
| FIG.2D |

CAGTCATCATGGCGAACCTTGGCTACTGG
CTGCTGGCCCTCTCTTTGTGACTATGTGTCGGCCTCTGCAAAAA
GCGGCCAAAGCCTGGAGGGTGGAACACCGGTGGAAGTCGGTATCCCGGGC
AGGGAAGCCCTGGAGGCAAACCGTTACCCACCTCAGGGTGGCACCCTGGGGG
CAGCCCCACGGTGTGGGCTGGGGACAACCCCATGGGGGCAGCTGGGACA
ACCTCATGGGTAGTTGGGGTCAGCCCCATGGCGGTGGATGGGGCCAAG
GAGGGGGTACCCATAATCAGTGGAACAAGCCCAGCAAAACCAAC
CTCAAGCATGTGGCAGG..........GGGTGGCCT

TGGTGGCTACATGCTGGGGAGGCGCCATGAGCAGGCCCATGATCCATTTTG
GCAACGACTGGGAGGACCGCTACTACCGTGAAAACATGTACCGCTACCCT
AACCAAGTGTACTACAGGCCAGTGGATCAGTACACAGCAACAAGAACAACTT
CGTGCACGACTGCGTCAATATCACCATCAAGCAGCACACGGTCACCACCA
CCACCAAGGGGAGAACTTCACCGAGACCGATGTGAAGATGATGGAGCGC
GTGGTGGAGCAGATGTGCGTCACCCAGTACCAGAAGGAGTCCCAGGCCTA
TTACGACGGGAGAAGATCCAGCACCGTGCTTTTCTCCTCCCTCCT
TCATCCCTCCCTCATCTTCCTTCCCTGATCGTGGGATGAGGG

FIG.4B

SEQUENCE LISTING

```
<160> NUMBER OF SEQ ID NOS:  4

<210> SEQ ID NO 1
<211> LENGTH: 752
<212> TYPE: DNA
<213> ORGANISM: Artificial Sequence
<220> FEATURE:
<223> OTHER INFORMATION: Description of Artificial Sequence:
      PrP[delta]H1

<400> SEQUENCE: 1
cagtcatcat ggcgaacctt ggctactggc tgctggccct ctttgtgact atgtggactg     60
atgtcggcct ctgcaaaaag cggccaaagc ctggagggtg gaacaccggt ggaagtcggt    120
atcccgggca gggaagccct ggaggcaacc gttacccacc tcagggtggc acctgggggc    180
agccccacgg tggtggctgg ggacaacccc atgggggcag ctggggacaa cctcatggtg    240
gtagttgggg tcagccccat ggcggtggat ggggccaagg agggggtacc cataatcagt    300
ggaacaagcc cagcaaacca aaaaccaacc tcaagcatgt ggcagggggt ggccttggtg    360
gctacatgct ggggagcgcc atgagcaggc ccatgatcca ttttggcaac gactgggagg    420
accgctacta ccgtgaaaac atgtaccgct accctaacca agtgtactac aggccagtgg    480
atcagtacag caaccagaac aacttcgtgc acgactgcgt caatatcacc atcaagcagc    540
acacggtcac caccaccacc aagggggaga acttcaccga gaccgatgtg aagatgatgg    600
agcgcgtggt ggagcagatg tgcgtcaccc agtaccagaa ggagtcccag gcctattacg    660
acgggagaag atccagcagc accgtgcttt tctcctcccc tcctgtcatc ctcctcatct    720
ccttcctcat cttcctgatc gtgggatgag gg                                  752

<210> SEQ ID NO 2
```

```
<211> LENGTH: 900
<212> TYPE: DNA
<213> ORGANISM: mouse prion

<400> SEQUENCE: 2
aattccttca gaactgaacc atttcaaccg agctgaagca ttctgccttc ctagtggtac      60
cagtccaatt taggagagcc aagcagacta tcagctatca tggcgaacct tggctactgg    120
ctgctggccc tctttgtgac tatgtggact gatgtcggcc tctgcaaaaa gcggccaaag    180
cctggagggt ggaacaccgg tggaagccgg tatcccgggc agggaagccc tggaggcaac    240
cgttacccac ctcagggtgg cacctggggg cagccccacg gtggtggctg ggacaaccc    300 catggggca gctggggaca acctcatggt ggtagttggg gtcagcccca tggcggtgga    360
tggggccaag gagggggtac ccataatcag tggaacaagc ccagcaaacc aaaaaccaac    420
ctcaagcatg tggcagggc tgcggcagct ggggcagtag tggggggcct tggtggctac    480
atgctgggga gcgccatgag caggcccatg atccattttg caacgactg ggaggaccgc    540 tactaccgtg aaaacatgta ccgctaccct aaccaagtgt actacaggcc agtggatcag    600
tacagcaacc agaacaactt cgtgcacgac tgcgtcaata tcaccatcaa gcagcacacg    660
gtcaccacca ccaccaaggg ggagaacttc accgagaccg atgtgaagat gatggagcgc    720
gtggtggagc agatgtgcgt cacccagtac cagaaggagt cccaggccta ttacgacggg    780
agaagatcca gcagcaccgt gcttttctcc tcccctcctg tcatcctcct catctccttc    840
ctcatcttcc tgatcgtggg atgagggagg ccttcctgct tgttccttcg cattctcgtg    900

<210> SEQ ID NO 3
<211> LENGTH: 772
<212> TYPE: DNA
<213> ORGANISM: Artificial Sequence
<220> FEATURE:
<223> OTHER INFORMATION: Description of Artificial Sequence:
      PrP[delta]H1 92 to 867

<400> SEQUENCE: 3
cgtccagtca tcatggcgaa ccttggctac tggctgctgg ccctctttgt gactatgtgg      60
actgatgtcg gcctctgcaa aaagcggcca agcctggag gtggaacac cggtggaagt    120 cggtatcccg ggcagggaag ccctggaggc aaccgttacc cacctcaggg tggcacctgg    180
gggcagcccc acggtggtgg ctggggacaa ccccatgggg gcagctgggg acaacctcat    240
ggtggtagtt ggggtcagcc ccatggcggt ggatgggggcc aaggaggggg tacccataat    300
cagtggaaca gcccagcaa accaaaaacc aacctcaagc atgtggcagg gggtggcctt    360
ggtggctaca tgctggggag cgccatgagc aggcccatga tccattttgg caacgactgg    420
gaggaccgct actaccgtga aaacatgtac cgctacccta accaagtgta ctacaggcca    480
gtggatcagt acagcaacca gaacaacttc gtgcacgact gcgtcaatat caccatcaag    540
cagcacacgg tcaccaccac caccaagggg gagaacttca ccgagaccga tgtgaagatg    600
atggagcgcg tggtggagca gatgtgcgtc acccagtacc agaaggagtc ccaggcctat    660
tacgacggga gaagatccag cagcaccgtg cttttctcct cccctcctgt catcctcctc    720
atctccttcc tcatcttcct gatcgtggga tgagggagct cggtacccgg gg         772

<210> SEQ ID NO 4
<211> LENGTH: 8
<212> TYPE: PRT
<213> ORGANISM: mouse prion
```

-continued

```
<400> SEQUENCE: 4

Ala Ala Ala Ala Gly Ala Val Val
  1               5
```

PRION PROPAGATION INHIBITION BY DOMINANT-NEGATIVE PRION PROTEIN MUTANTS

The present invention relates to a vector having a nucleic acid insert coding for a mutated prion protein, a mutated prion protein, a DNA coding for such a protein and a process for the preparation thereof. Furthermore, this invention concerns antibodies, a vaccination agent and the use of the above-mentioned subject matters. Moreover, the present invention relates to non-human mammals, e.g. working animals, which are resistant to prion infections.

The prion diseases which have spread in the past few years and include inter alia BSE, Creutzfeldt-Jakob disease and scrapie, represent a group of absolutely fatal neurodegenerative diseases in human beings and animals which are caused by infectious pathogens whose structure is still unclear and which are referred to as "prions" below. For the time being there are no satisfactory possibilities regarding the prophylaxis and/or treatment of these diseases. The development of such prophylaxis/treatment possibilities is made more difficult because the molecular pathogenesis of prion diseases is presently not clarified to a sufficient extent. Only a slight delay of the prion replication has been achieved by means of various drugs so far, but the infection could by no means be brought to a stand-still (Priola et al., Inhibition of scrapie-associated PrP accumulation. Probing the role of glycosaminoglycans in amyloidogenesis, Mol. Neurobiol. 8, pp. 113–120 (1994). Furthermore, such a treatment is accompanied by considerable side-effects, which is due to the fact that these drugs only have a very unspecific effect.

Therefore, it is the object of the present invention to provide a product serving for rendering working animals whose tissues or products are used as foodstuffs, drug constituents or cosmetics for human use resistant to prion propagation and protecting infected human or animal individuals from the onset of the infection and the progression thereof, respectively.

According to the invention this is achieved by the subject matters defined in the claims.

Thus, the subject matter of the present invention relates to a vector containing a nucleic acid insert coding for a mutated prion protein, the mutated prion protein having an insertion, substitution and/or deletion within the H1 region. It should preferably be a vector suitable for gene prophylaxis and gene therapy, respectively.

On the basis of this invention the inventors modified critical regions, e.g. the Helix1 region (H1) (Gasset et al., Predicted alpha-helical regions of the prion protein when synthesized as peptides form amyloid, Proc. Natl. Acad. Sci. USA 89, p. 10940, 1992) in the prion protein by means of genetic technique by carrying out e.g. mutations in the form of insertions, substitutions or deletions, particularly deletions. In this connection, the inventors found out that these modified recombinant proteins lose their capability of being convertible into the amyloid-like, disease-associated form of the prion protein ($PrP^{Sc}$). In addition, it was found that the presence of the mutated proteins has an inhibitory effect on the conversion of the endogenous wild-type prion protein ($PrP^c$) which is naturally present in the organism into the disease-associated form ($PrP^{Sc}$) (what is called dominant-negative effect).

The expression "vector suitable for gene therapy" comprises any vector which is suitable for the gene transfer, i.e. the introduction of nucleic acids into cells. The vector may remain episomally within the cells or be integrated into the genome. Furthermore, the vector may be a plasmid vector or viral vector. Examples of viral vectors are retroviral, herpes simples virus, cytomegaly virus (CMV), adenovirus, vaccinia virus or adeno-associated virus (AAV) vectors. pUC18 or pUC19 have to be mentioned as preferred plasmid vectors.

The expression "mutated prion protein" comprises a prion protein which as compared to the wild-type has been modified as regards its function and/or its length by means of suitable measures with which a person skilled in the art is sufficiently familiar. This may be done e.g. by inserting mutations on a nucleic acid level, e.g. by carrying out insertions, substitutions and particularly deletions. Methods of producing the above modifications within the nucleic acid sequence are known to the person skilled in the art and described in standard works of molecular biology, e.g. in Sambrook et al., Molecular Cloning: A Laboratory Manual, $2^{nd}$ edition, Cold Spring Harbor Laboratory Press, Cold Spring Harbor N.Y. (1989). The mutation is carried out within the H1 region of the prion protein within which an accumulation of identical amino acids occurs (Ala-Gly-Ala-Ala-Ala-Ala-Gly-Ala) and which is conserved with all animal species. As to the sequences of the prion proteins of various organisms reference shall be made to Prusiner, S. B., Molecular structure, biology and genetics of prions, Adv. Virus Res. 35, p. 83 et seq. (1988); Schätzl, H. M. et al., Prion protein gene variation among primates, J. Mol. Biol. 245, p. 362 et seq. (1995) and Gabriel, J. M. et al., Molecular cloning of a candidate chicken prion protein, Proc. Natl., Acad. Sci. USA 89, p. 9097 et seq. (1992). In a particularly preferred embodiment, the modification concerns amino acids 108–121 (based on the mouse PrP sequence), preferably 112–121, most preferably 114–121. This modification must usefully cover more than one amino acid, i.e. at least two, since otherwise the described properties such as the non-convertibility into the disease-associated form of the prion protein ($PrP^{Sc}$) and/or the trans-dominant inhibition of the accumulation of wild-type $PrP^{Sc}$ cannot be expected. Since as proved the region of amino acids 112 to 121, preferably 114 to 121, contains the strongest amyloidogenic amino acids of the prion protein, a deletion is the preferred route of preparing a modified protein comprising the above-mentioned properties. Following the deletion of at least two of the amyloidogenic amino acids in the above-mentioned region, another route is the substitution by amino acids which are known to have no tendency of forming a β-pleated sheet structure or can even destroy an existing β-pleated sheet structure (e.g. proline). The direct insertion of amino acids which counteract the formation of a β-pleated sheet structure, e.g. proline, is also conceivable. Another advantageous modification of the prion protein is made at the carboxy terminus. The already spontaneously occurring secretion of PrP molecules is enhanced by this modification (Borchelt et al., Release of the cellular prion protein from cultured cells after loss of its glycoinositol phospholipid anchor, *Glycobiology* 3, pp. 319–329 (1993). This is achieved according to the invention in that mutated prion proteins are secreted to an increased extent by the producing cells by a lack of glycoinositol phospholipid anchor. Thus, it is possible to reach by diffusion also those cells in spatial neighborhood which do not express the mutated prion protein per se. As a result, the desired dominant negative effect is expanded to a much greater number of target cells.

The expression "nucleic acid insert" comprises any nucleic acid such as DNA or RNA which codes for a mutated prion protein. It is favorable for the nucleic acid insert to be expressible, e.g. when it is controlled by a constitutive or inducible promoter. A nucleic acid insert in the form of a DNA which comprises the following is preferred:

(a) the DNA of FIG. 4 or a DNA differing therefrom by one or several base pairs, (b) a DNA hybridizing with the DNA from (a), or (c) a DNA related to the DNA from (a) or (b) via the degenerated genetic code.

The expression "hybridizing DNA" refers to a DNA which hybridizes with a DNA from (a) under conventional conditions, particularly at 20° C. below the melting point of the DNA. In this connection, the term "hybridizing" refers to conventional hybridization conditions, preferably to hybridization conditions where 5×SSPE, 1% SDS, 1×Denhardts solution are used as the solution and the hybridization temperatures are between 35° C. and 70° C., preferably 65° C. After the hybridization washing is preferably carried out first with 2×SSC, 1% SDS and then with 0.2×SSC at temperatures between 35° C. and 70° C., preferably at 65° C. (for the definition of SSPE, SSC and Denhardts solution see Sambrook et al., supra). Stringent hybridization conditions as described e.g. in Sambrook et al., supra, are particularly preferred.

According to the invention an above nucleic acid insert is inserted in an above vector. The insertion is made such that the nucleic acid fragment can be expressed. This can be achieved by inserting in phase the nucleic acid fragment in an expression unit present in the vector. To this end, it may be necessary to at least partially remove a DNA present in the expression unit. It may also be advantageous to replace elements of the existing expression unit, such as enhancers, promoters or polyadenylation site, at least partially by others. A promoter which is specific to a tissue kind is preferably inserted in an expression unit, so that the expression of the nucleic acid insert which is controlled by the promoter becomes tissue-specific. The above nucleic acid insert can also be expressed in an expression unit which must be introduced into the vector for this purpose. In order to express the mutated prion protein according to the invention, the vector is transformed into suitable cells. Examples of such cells comprise the *E. coli* strains HB101, DH1, x1776, JM101, JM109, BL21 and SG13009, the yeast strain *Saccharomyces cerevisiae* and the animal cells Neuro 2a, 3T3, FM3A, CHO and COS. Moreover, the person skilled in the art is familiar with conditions of culturing transformed cells and transfected cells, respectively. He also knows methods of isolating and purifying the protein expressed by the nucleic acid insert (particularly by the DNA). Such a protein and fragments thereof also form a subject matter of the present invention.

In the case of virus vectors, it often proves to be favorable to insert the nucleic acid fragment in an expression unit present in the vector. The possibly accompanying removal or partial removal of virus DNA present in the expression unit then results in a virus vector which has a defect in a viral function. This defect can be used as a selection marker. On the other hand, the defect can be compensated, if necessary, by common methods such as complementation in trans. Virus vectors in which the nucleic acid fragment is inserted such that the virus vectors per se are no longer capable of forming infectious wild-type viruses are preferred according to the invention.

Common methods can be carried out for the preparation of an above vector. In a preferred embodiment, the vector according to the invention is pUC-PrPΔH1 or pCMV-PrPΔH1. The latter was deposited as *E. coli* culture with the DSMZ Braunschweig (*Deutsche Sammlung von Mikroorganismen und Zellkulturen GmbH* [German-type collection of microorganisms and cell cultures], Mascheroder Weg 1b, 38124 Braunschweig) under number DSM 11400 on Feb. 6, 1997. The preparation of the pCMV-PrPΔH1 vector is described in Example 1 below. The PrPΔH1 (SEQ ID NO:1) insert used for this purpose (nucleic acid fragment) originates from the mouse prion protein gene and codes for a mutated protein which is 8 amino acids shorter than the wild type. The deletion was inserted in the wild-type gene by means of site directed mutagenesis and is found from positions 438 to 461 (based on the counting according to Locht et al., Proc. Natl. Acad. Sci USA 83, p. 6372 (1986), i.e. within the H1 region of the prion protein and relates to amino/acids (Ala-Ala-Ala-Ala-Gly-Ala-Val-Val [amino acids 114–121](SEQ ID NO:8). A sequence comparison between the mouse wild-type gene and the employed insert PrPΔH1 is shown in FIG. 2 (SEQ ID NO: 2). The DNA sequence of PrPΔH1 is shown additionally in FIG. 4 (SEQ ID NO: 1). The second above-mentioned vector pUC-PrPΔH1 according to the invention was prepared by cloning the PrPΔH1 insert according to FIG. 4 (SEQ ID NO: 1) into pUC19 via AatII/SacI.

A further subject matter of the present invention relates to an antibody directed against an above protein. Such an antibody can be prepared by common methods. It may be polyclonal or monoclonal. For its preparation it is favorable to immunize animals—particularly rabbits or chickens for a polyclonal antibody-and mice for a monoclonal antibody—with an above protein or with fragments thereof. Further boosters of the animals can be made with the same protein or with fragments thereof. The polyclonal antibody can then be obtained from animal serum and egg yolk, respectively. For the preparation of the monoclonal antibody animal spleen cells are fused with myeloma cells.

The above subject matters are particularly suitable to provide a prophylaxis and/or treatment in the case of prion diseases. In this connection, one makes use of the effect that the mutated prion proteins cannot be converted into the infectious form, on the one hand, and that by overexpression of the mutated prion proteins existing cellular wild-type prion proteins (PrP$^c$) are prevented from converting into PrP$^{Sc}$, on the other hand. In the latter case, it is recommended that the PrP mutation be carried out on the PrP DNA sequence of the target species analogously to ensure the strongest possible protein-protein interaction between PrP$^c$ and PrP$^{Sc}$ which is necessary for the desired inhibitory effect. Prophylaxis of prion diseases is effected e.g. by the production of transgenic working animals which carry a mutated PrP gene either exclusively or in addition to the endogenous wild-type PrP gene. A person skilled in the art knows suitable transgenesis methods. For example, efficient methods of producing transgenic cattle by the insertion of foreign (additional) genes are available (Hyttinen et al., "Generation of transgenic dairy cattle from transgene-analyzed and sexed embryos produced in vitro", Biotechnology N.Y., 12, pp. 606–608, 1994). In addition, reference is made to the mechanism of the homologous recombination (cf. R. M. Torres, R. Kühn, Laboratory Protocols for Conditional Gene Targeting, Oxford University Press, 1997) in embryonic stem cells (e.g. mouse 129/SV) and new and obviously very efficient nuclear transfer technology (E. Pennisi, "After Dolly, a Pharming Frenzy", Science 279, pp. 646–648, 1998), respectively. The homologous recombination between the DNA sequences present in a chromosome and the new, added cloned DNA sequences enables the insertion of a cloned gene in the genome of a living cell in place of the original gene. By means of this method it is possible to obtain animals which are homozygotic for the desired gene or the desired gene portion or the desired mutation, via chimeras using embryonic stem cells.

Furthermore, double-transgenic mammal models can be produced by crossbreed of the transgenic mammal according to the invention with already established transgenic mammals.

A gene substitution vector (e.g. on the basis of the above described plasmid pCMV-PrPΔH1) and an embryonic stem cell line of the corresponding non-human mammal (ES 129/SV is preferred in the case of a mouse, for example) are used for the production of a transgenic mammal according to the invention via the mechanism of the gene exchange. In this connection, the resulting recombinant clones of the embryonic stem cells are injected into blastocytes which are then implanted into suitably prepared female animals for the production of chimeras. Here, "suitably prepared female animals" means that the animals have been prepared by various measures, e.g. by a hormone treatment, for their task of carrying to full term. In this connection, reference is also made to "R. M. Torres, R. Kühn, see above". Since it is advantageous to have available homozygotic animals, the resulting heterozytogic strains can then be mated with another animal of the same strain or another (heterozygotic) strain. Thus, a homozygotic condition can be reached by cross-breed. This serves for producing prion-resistant animals which can subsequently be further bred according to standard methods.

The gene therapy of prion diseases in human or animal individuals can be made by transfection and transduction, respectively, of somatic cells of the corresponding organism, such as neurons, gliacytes, fibroblasts or cells of the cerebral blood vessels, with the vector according to the invention. The transduction can be carried out according to common methods. If the vector is present as viral particle, it will be favorable to infect the cells therewith. On the other hand, if it is present as a nucleic acid, e.g. DNA, it will be advisable to transfect the cells therewith. For example, electroporation, calcium-phosphate co-precipitation, lipofection and particle gun have to be mentioned as transfection techniques. The cells may be present in the organism. On the other hand, the cells to be transduced can also be isolated from the organism, be transduced outside the organism and returned into the organism again. Such cells are referred to as autologous cells. In addition, it is also possible to use allogenic cells for the transduction as regards the organism. In this connection, it is favorable for these cells to belong to an HLA type corresponding to the organism.

A further subject matter of the invention relates to a vaccination agent which comprises an above vector, an above protein or fragments thereof and conventional auxiliary agents, such as buffers, diluents, carriers, etc.

By means of the present invention it is possible to stop the onset of a prion infection within the meaning of a prophylaxis and prevent the progression of such infections in already infected individuals, respectively. On the one hand, it is possible to eliminate the risk of an infection of human beings via the food chain, via animal-derived pharmaceutical preparations and cosmetics, respectively, by the production of transgenic working animals (e.g. cattle, sheep, goats, pigs, chickens, fish) which by carrying the mutated PrP gene are protected from a prion infection from the very beginning. On the other hand, the present invention enables to prevent and treat, respectively, an otherwise fatal disease via an in vivo gene therapy and ex vivo gene therapy, respectively.

As compared to a conventional treatment, a gene therapy/prophylaxis has various advantages which are based on the specificity of the molecular point of attack (e.g. interference in the protein-protein interaction between $PrP^c$ and $PrP^{Sc}$). The freedom from side-effects and simultaneous high degree of efficiency also result therefrom. A gene therapy/prophylaxis can be made as follows:

1) Production of prion-resistant working animals: the vector according to the invention serves for producing transgenic animals which in place of the endogenous wild-type $PrP^c$ or in addition to the endogenous wild-type $PrP^c$, express a mutated prion protein which per se can no longer be converted into a protease-resistant $PrP^{Sc}$ form and can additionally prevent the conversion from wild-type $PrP^c$ into $PrP^{Sc}$. As compared to transgenic "knockout" animals, i.e. animals which express no prion protein at all, the transgenic animals which express the mutated form have the advantage that no phenotypic differences occur with respect to "normal animals", since animals having a mutated prion protein modified in only one small region certainly still contain the normal physiological functions of the prion protein. The infection of these transgenic animals and thus another spread of e.g. the BSE epidemic would be prevented in working animals by means of this gene prophylaxis.
2) Artificial insemination/in vitro fertilization: sperm from a transgenic prion-resistant working animal, e.g. cattle, is used to produce further generations of resistant working animals by means of the artificial insemination route common for breeding working animals today. An in vitro fertilization is also considered preferably, since it offers the advantage of investigating the embryos for their genetic state, particularly the presence of the transgene, even before they are implanted into the uterus.
3) ex vivo gene therapy: Autologous cells from a patient, which can be implanted e.g. into the central nervous system are removed and transfected and transduced, respectively, with the vector according to the invention as cell culture and reimplanted into the patient.
4) in vivo gene therapy: A vector according to the invention (e.g. a recombinant virus) with an open reading frame of a mutated prion protein and suitable control elements (e.g. promoters, enhancers, polyadenylation signal, etc.) is used to directly infect the affected cells (e.g. nerve cells) thus preventing the spread of a disease within the CNS.

The invention is described by means of the figures showing:

FIG. 1: eukaryotic expression vector pL15TK

The abbreviations used have the following meanings:

HCMV Prom.: human cytomegalovirus promoter/enhancer
AMP: ampicillin resistance gene
Z: part of the Lac operon
I: part of the Lac operon
(TK) poly A: polyadenylation signal of the herpes simplex virus thymidine kinase gene
ori: bacterial replication origin as well as the common abbreviations for the restriction sites, FIG. 2: a sequence comparison between the DNA sequence for wild-type mouse prion protein (SEQ ID NO:2)

(Locht et al., Proc. Natl. Acad. Sci. USA 83, p. 6372 (1986); upper row) and the employed insert PrPΔH1 (SEQ ID NO: 3) (nucleotides 92 to 867; lower row)

"silent": silent mutation which causes no difference on an amino acid level

☐=start codon and stop codon, respectively

Figure 3:
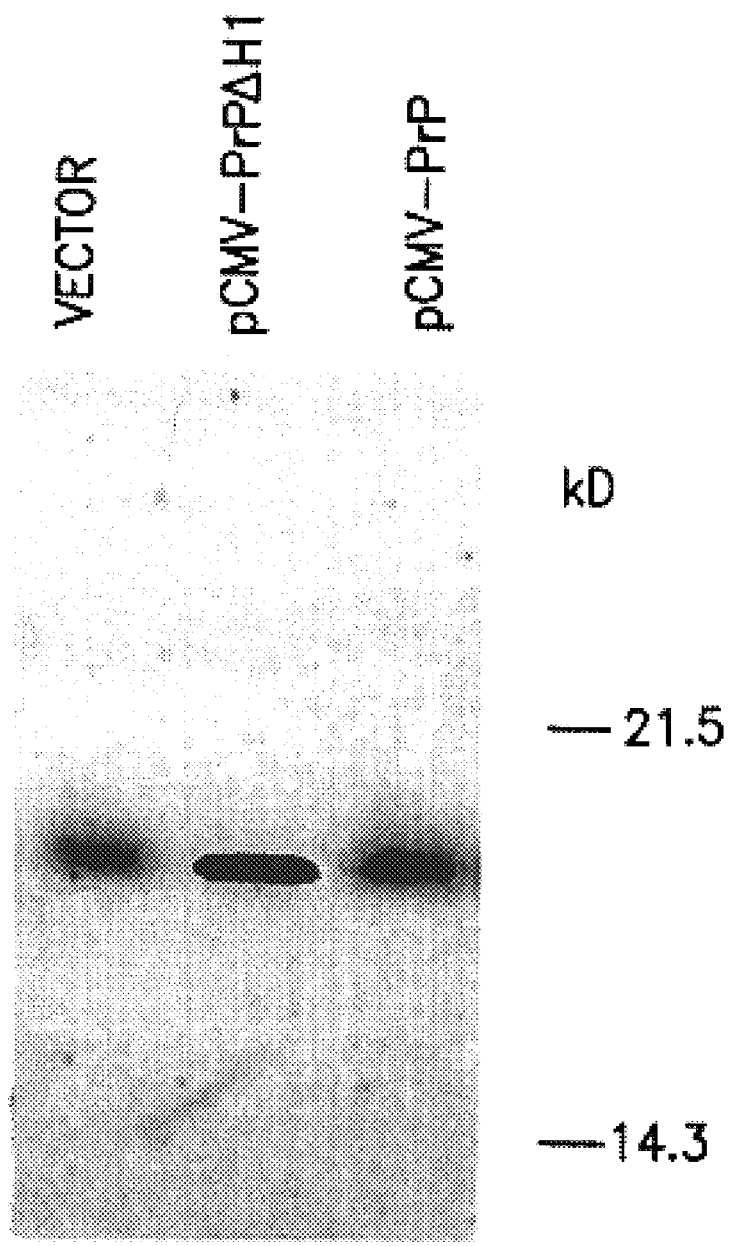

FIG. 3: Western blot after transient transfection of mouse neuroblastoma cells which were infected persistently with mouse scrapie pathogens, using vector (pL15tk)=control (empty vector)
pCMV-PrPΔH1 (according to the invention)
pCMV-PrP (wild-type).

FIG. 4: DNA sequence of the PrPΔH1 (SEQ ID NO:1) insert

☐=start codon and stop codon, respectively

The invention is further explained by the below examples:

EXAMPLE 1

Preparation of a Vector which Contains an Insert for a Mutated Prion Protein The deposited vector pCMV-PrPΔH1 was prepared using the pL15TK expression vector. This vector is based on pUC19 and contains the human CMV promoter as well as the HSV-TK polyadenylation signal. The gene map of this vector is shown in FIG. 1. The PrPΔH1 insert was cloned in by making the sticky ends of the insert, which had been excised by restriction endonucleases AatII and SacI, blunt using T4-DNA polymerase and then ligating it into the SmaI restriction site of pL15TK.

EXAMPLE 2

Western Blot

The pCMV-PrPΔH1 plasmid is transfected into mouse neuroblastoma cells which are infected in persistent way with the mouse scrapie pathogen (Race et al., Characterization of scrapie infection in mouse neuroblastoma cells, J. gen. Virol. 68, pp. 1391–1399 (1987)). After about 48 hours, the cells are lyzed for the production of cytoplasmic extracts after about 48 hours and analyzed in a Western blot after limited proteinase K digestion, guanidine-isothiocyanate denaturation and peptide digestion: N glycosidase F (PNGase F). The result obtained in the Western blot is shown in FIG. 3. This Western blot proves the non-convertibility of the mutant PrPΔH1 into $prp^{Sc}$ and its dominant-negative effect. The extent of the dominant-negative effect is shown by a comparison of the $prp^{Sc}$ amounts which formed when the pCMV-PrPΔH1 vector was used (FIG. 3, lane 2) with extracts from persistent infected cells which were only transfected with the empty vector (FIG. 3, lane 1).

What is claimed is:

1. A vector comprising a nucleic acid insert encoding a mutated prion protein, wherein:
   (a) a mutation of the mutated prion protein consists of an alteration of two or more amino acids within the H1 region, the alteration consisting of one or more insertions, substitutions and/or deletions within the region of amino acids 112–121 of wild type prion protein, with the proviso that such alteration does not include deletion of the entire region of amino acids 112–121; and
   (b) the mutated prion protein exhibits the following properties:
      (i) an inability to convert to a disease-associated form of prion protein under physiological conditions; and
      (ii) an inhibitory effect on the conversion of wild-type prion protein into a disease-associated form of prion protein.

2. The vector according to claim 1 wherein the vector is a viral or plasmid vector.

3. An isolated host cell comprising and expressing the vector of claim 2 to produce the mutated prion protein.

4. The vector according to claim 1 wherein the vector is a viral vector selected from the group consisting of: AAV, Herpes simplex virus, retrovirus, adenovirus, and Vaccinia virus.

5. An isolated host cell comprising and expressing the vector of claim 4 to produce the mutated prion protein.

6. The vector according to claim 1 wherein the nucleic acid insert comprises a DNA selected from the group consisting of:
   (a) the DNA of SEQ ID NO:1, and
   (b) a DNA differing from the DNA of FIG. 4 by one or more base pairs which would effect an alteration in two or more amino acids within the region encoding amino acids 112–121 of wild type prion protein.

7. The vector of claim 1 wherein the alteration of the H1 region consists of deletion of amino acids 114–121.

8. An isolated cell comprising and expressing the vector of claim 7.

9. A vector comprising a nucleic acid insert encoding a mutated prion protein, wherein the mutated prion protein:
   (a) comprises an alteration of two or more amino acids within the H1 region, the alteration consisting of one or more insertions, substitutions and/or deletions within the region of amino acids 112–121 of wild type prion protein,
   (b) exhibits the following properties:
      (i) an inability to convert to a disease-associated form of prion protein under physiological conditions; and
      (ii) an inhibitory effect on the conversion of wild-type prion protein into a disease-associated form of prion protein,
   wherein the vector is pCMV-PrPΔH1 deposited with the Deutsche Sammlung Von Mikroorganism und ZellKulturen under number DSM 11400 in accordance with the provisions of the Budapest Treaty.

10. An isolated host cell comprising and expressing a vector producing a mutated prion protein, wherein said vector comprises a nucleic acid insert encoding the mutated prion protein, and wherein the mutated prion protein:
   (a) comprises an alteration of two or more amino acids within the H1 region, the alteration consisting of one ore more insertions, substitutions and/or deletions within the region of amino acids 112–121 of wild type prion protein,
   (b) exhibits the following properties:
      (i) an inability to convert to a disease-associated form of prion protein under physiological conditions; and
      (ii) an inhibitory effect on the conversion of wild-type prion protein into a disease-associated form of prion protein,
   wherein the vector is pCMV-PrPΔH1 deposited with the Deutsche Sammlung Von Mikroorganism und ZellKulturen under number DSM 11400 in accordance with the provisions of the Budapest Treaty.

11. An isolated host cell comprising a vector comprising a nucleic acid insert encoding a mutated prion protein, and wherein the mutated prion protein:
   (a) comprises an alteration of two or more amino acids within the H1 region, the alteration consisting of one ore more insertions, substitutions and/or deletions within the region of amino acids 112–121 wild type prion protein,
   (b) exhibits the following properties:
      (i) an inability to convert to a disease-associated form of prion protein under physiological conditions; and
      (ii) an inhibitory effect on the conversion of wild-type prion protein into a disease-associated form of prion protein,
   wherein the vector is pCMV-PrPΔH1 deposited with the Deutsche Sammlung Von Mikroorganism und ZellKulturen under number DSM 11400 in accordance with the provisions of the Budapest Treaty.

12. A process for producing a mutated prion protein, such process comprising culturing a transformant comprising a vector comprising a nucleic acid insert encoding the mutated prion protein, wherein:
   (a) a mutation of the mutated prion protein consists of an alteration of two or more amino acids within the H1 region, the alteration consisting of one or more insertions, substitutions, and deletions within the region of amino acids 112–121 of the prion protein, with the proviso that such alteration does not include deletion of the entire region of amino acids 112–121; and
   (b) exhibits the following properties:
      (i) an inability to convert to a disease-associated form of prion protein under physiological conditions; and
      (ii) an inhibitory effect on the conversion of wild-type prion into a disease-associated form of prion protein.

13. An isolated DNA comprising the nucleotide sequence of SEQ ID NO:1.

14. The vector according to claim 6, wherein the alteration in the amino acids is selected from the group consisting of
   (i) substitution by amino acids which do not form a β-pleated structure;
   (ii) substitution by amino acids that destroy an existing β-pleated structure;
   (iii) insertion of amino acids which counteract the formation of a β-pleated structure; and
   (iv) deletion of at least two of the amyloidogenic amino acids within the region of amino acids 112–121 of wild type prion protein.

* * * *

UNITED STATES PATENT AND TRADEMARK OFFICE
CERTIFICATE OF CORRECTION

PATENT NO. : 6,593,105 B1
DATED : July 15, 2003
INVENTOR(S) : Holscher et al.

It is certified that error appears in the above-identified patent and that said Letters Patent is hereby corrected as shown below:

Column 4,
Line 13, "amino/acids" should be -- amino acids --.
Line 14, "NO:8)" should be -- NO:4) --.

Column 6,
Line 56, "promoter/enhancer" should be -- promoter/-enhancer --.

Column 8,
Lines 22 and 24, "prp$^{Sc}$" should be -- PrP$^{sc}$ --.

Signed and Sealed this

Eleventh Day of November, 2003

JAMES E. ROGAN
*Director of the United States Patent and Trademark Office*